United States Patent [19]

Weissman

[11] Patent Number: 4,459,107

[45] Date of Patent: * Jul. 10, 1984

[54] DENTAL IMPRESSION TRAY AND METHOD OF USE

[75] Inventor: Bernard Weissman, New York, N.Y.

[73] Assignee: IPCO Corporation, White Plains, N.Y.

[*] Notice: The portion of the term of this patent subsequent to Jan. 11, 2000 has been disclaimed.

[21] Appl. No.: 376,520

[22] Filed: May 10, 1982

Related U.S. Application Data

[63] Continuation-in-part of Ser. No. 269,341, Jun. 1, 1981, Pat. No. 4,368,040.

[51] Int. Cl.³ .................................................. A61C 9/00
[52] U.S. Cl. ...................................... 433/36; 433/213; 433/223
[58] Field of Search .................... 433/24, 34, 36, 37, 433/41, 45, 46, 47, 213, 214, 215, 217, 223; 264/16, 17, 18, 19

[56] References Cited

U.S. PATENT DOCUMENTS

| | | | |
|---|---|---|---|
| 508,677 | 11/1893 | Burlingame | 433/47 |
| 1,179,317 | 4/1916 | Hurrey | 433/47 |
| 1,489,192 | 4/1924 | Cleveland | 433/45 |
| 1,561,052 | 11/1925 | Brown | 433/37 |
| 2,337,036 | 12/1943 | Erdle | 433/34 |
| 2,529,429 | 11/1950 | Spiro | 433/41 |
| 3,576,075 | 4/1971 | Scott | 433/34 |
| 3,878,610 | 4/1975 | Coscina | 433/37 |
| 3,978,585 | 9/1976 | Holcomb | 433/41 |
| 4,080,736 | 3/1978 | Kennedy | 433/36 |
| 4,368,040 | 1/1983 | Weissman | 433/36 |

Primary Examiner—John J. Wilson
Attorney, Agent, or Firm—Goodman & Teitelbaum

[57] ABSTRACT

A dental impression tray for forming a dental prosthesis, the dental tray including a trough-like configuration. A valve device is provided for adjustable placement within slots in the outer walls of the tray, the valve device being suitably placed with respect to a mold cavity defined within the tray. The tray is placed over a positive restored model of dental area and a negative impression is formed in the tray. The restored area is then removed from the positive model and the tray is replaced onto the unrestored model. The mold cavity is defined between the negative impression and the unrestored dental model. Casting material is then inserted through the valve device to form a dental prosthesis, which can be used directly as the final prosthesis, or can be used as a model for further forming of the final dental prosthesis.

20 Claims, 17 Drawing Figures

DENTAL IMPRESSION TRAY AND METHOD OF USE

CROSS-REFERENCE TO RELATED APPLICATION

This application is a continuation-in-part of Application Ser. No. 269,341, filed on June 1, 1981, and now U.S. Pat. No. 4,368,040, issued Jan. 11, 1983, by the present inventor for a Dental Impression Tray For Forming A Dental Prosthesis In Situ, the entire disclosure of which is herein incorporated by reference.

BACKGROUND OF THE INVENTION

This invention relates to dental impression trays, and more particularly to a method and apparatus for utilizing a dental impression tray in the formation of a dental prosthesis from a dental model.

In the formation of a dental prosthesis, numerous methods are well known in the art. Some of these methods include forming the prosthesis directly in the patient's mouth. While these methods have been quite successful, they place many limitations and restrictions upon the type of material that can be utilized, as well as the type of processing that can be carried out. For example, some material requires the use of high temperature in order to properly set. Polyvinylchloride, by way of example, requires a temperature of approximately 800° F. in order to properly set. Of course, such material could not be utilized in situ in the patient's mouth in the formation of the prosthesis occurs directly in the mouth area, not all types of prosthesis can be formed. Furthermore, it may provide an inconvenience or be uncomfortable for the patient, in some cases, to have the prosthesis formed directly in the mouth.

Other available prior art methods form the dental prosthesis outside of the patients mouth. These methods are time consuming, requiring the formation of numerous positive molds, cutting sections of each mold, properly fitting the cut sections from one mold to another, and ultimately utilizing one of these mold sections as the pattern for a final casting of the prosthesis.

Therefore, while there are presently numerous methods for forming such dental prosthesis, improvements would appear needed in connection with such methods and apparatus.

SUMMARY OF THE INVENTION

Accordingly, it is an object of the present invention to provide an improved method and apparatus for making a dental prosthesis.

Another object of the present invention is to provide a dental impression tray which can be used in conjunction with the formation of a dental prosthesis.

Still another object of the present invention is to provide an improved dental impression tray which permits utilization of the tray itself in the formation of a mold cavity for forming a dental prosthesis therein.

Yet another object of the present invention is to provide a method for utilizing a dental impression tray in the direct formation of a dental prosthesis from a dental model.

A further object of the present invention is to provide a dental impression tray which can facilitate the formation of a dental prosthesis directly from a dental model.

Briefly, in accordance with the present invention, there is provided a dental impression tray for use in forming a dental prosthesis. The tray is shaped in an arcuate fashion, having a substantially U-shaped cross sectional configuration. Suitable dental impression material is placed in the tray for the formation therein of a negative impression of the restored area of a dental model. Proper casting devices are provided in conjunction with the tray for adjustable placement on the tray with respect to a mold cavity defined between the negative impression formed in the tray and the unrestored dental model. These casting devices are also utilized for the application of casting material into the mold cavity.

In an embodiment of the invention, the casting devices include slots formed in the outer wall of the tray vices together with an open channel along such outer wall. Also included is an adjustable strap having apertures therein. The strap can be placed within the channel to position one of the apertures adjacent to the slot in the peripheral wall of the tray. A valve is inserted into the aperture. A removable plug is insertable into a central bore of the valve so as to extend up to a mold cavity defined between the negative impression and the unrestored model. This plug will form a sprue channel in the negative impression material. The tray can be formed as a one piece construction or can be formed from sections joined together to provide an integral tray unit.

The present invention also comprises a method for forming the dental prosthesis, including the initial formation of a positive dental model of the dental area to be restored. A restoration is then made on the positive model, and a negative impression of the restored area of the model is formed in a dental impression tray. The restoration is removed from the dental model. The dental impression tray is repositioned on the unrestored dental model so as to form a mold cavity between the negative impression and the dental model. Suitable dental casting material is injected into the mold cavity so as to form a dental prosthesis. The dental prosthesis is removed and can be either be used as the final dental prosthesis itself, or can be utilized as a temporary model in the formation of the final dental prosthesis, such as serving as the investment pattern for the casting of the final dental prosthesis.

BRIEF DESCRIPTION OF THE DRAWINGS

With the above and other additional objects and advantages in view, as will hereinafter appear, this invention comprises the devices, combinations, and arrangements of parts hereinafter described by way of example, and illustrated in the accompanying drawings of a preferred embodiment in which.

In the various figures of the drawing, like reference characters designate like parts.

DETAILED DESCRIPTION OF THE PREFERRED EMBODIMENTS

Referring now to FIGS. 1-4, the dental impression tray assembly of the present invention is shown to include a dental impression tray 10, an elongated strap 12, a one-way valve 14, and a sprue former 16. The dental impression tray 10 itself is formed in an arcuate form having a substantially U-shaped cross sectional configuration. The tray 10 includes a base wall 18 with a pair of upstanding sidewalls including an inner sidewall 20 and an outer sidewall 22. The sidewalls 20, 22 in conjunction with the base wall 18, define a trough-like configuration. The inner sidewall 20 is flared in an upwardly direction to facilitate easier utilization. The upper end of the inner wall 20 terminates in a reinforced rib 24 at its upper end. The upper end of the outer wall 22 terminates in an inwardly directed overhanging lip 26 to define a peripheral groove 28 along the inside of sidewall 22. At the proximate arcuate midsection of the outer wall 22, there is provided a notch 30.

Upwardly extending from the base wall 18 is a sloped surface 32 which rises towards the outer wall 22 and terminates in a vertical wall 34. Between the wall 34 and the inner surface of the outer sidewall 22, there is defined a peripheral groove 36.

The grooves 36 and 28 linearly extending along the entire inner periphery of the outer sidewall 22, to define therebetween a channel 38 having an open mouth. It should be noted, that a passageway is formed by the channel 38 which can receive the strap 12 so as to respectively position the strap adjacent to the interior surface of the sidewall 22.

Elongated locating slots 40 are positioned longitudinally along the outer sidewall 22. It should be noted, that the slots 40 are respectively coaligned with the channel 38. The inner sidewall 20 is noted to have an uninterrupted solid surface and thus does not contain any slots therein. It should be also noted, that the underside 42 of the base wall is substantially flat so as to provide a substantially flat bottom to the tray 10.

Laterally extending from the rear of the dental impression tray 10, is a handle 44 integrally formed with and extending from the base wall 18 of the tray. The handle 44 includes a coupling section 46 securing it to the bottom surface 42 of the tray and a tapered handle portion 48 adjacent the distal end for grasping of the tray. It should be noted that the handle 44 could be formed of a removable type, as is known heretofore.

Figure 2:
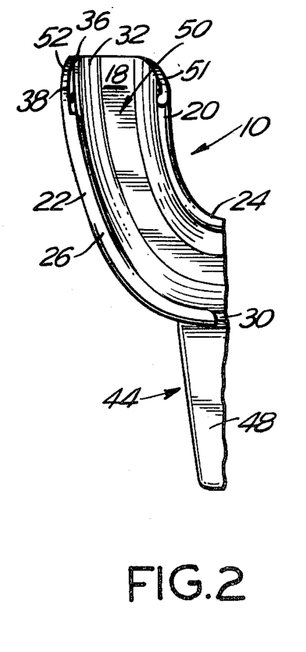
FIG. 2 is a fragmented top view of half of the dental impression tray shown in FIG. 1.
Figure 3:
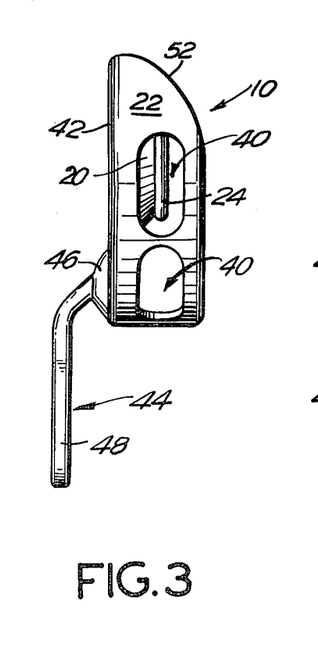
FIG. 3 is a side view of the dental impression tray shown in FIGS. 1 and 2.
Figure 4:
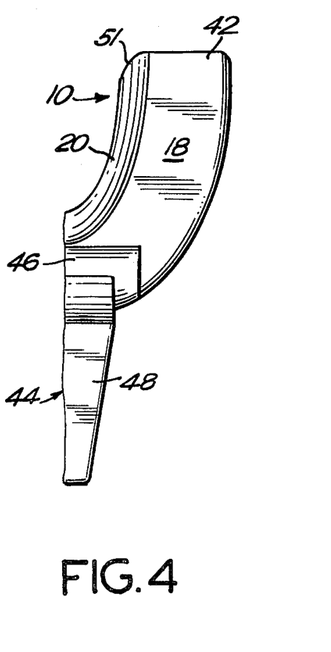
FIG. 4 is a fragmented bottom view of half of the dental impression tray shown in FIGS. 1-3.

The base wall 18, together with the upstanding sidewalls 20, 22, define a trough-like area 50 which can receive dental impression material of the type well-known in the dental art in the formation of negative impressions. As best shown in FIGS. 2 and 3, the forward distal ends of the inner and outer walls 20, 22 terminate in an arcuate edges 51, 52, and the rib and overhanging lip 24, 26 terminate at a distance spaced from the bottom distal end of the tray. The curved edge 52 facilitates in the insertion of the strap 12 within the channel 38 as will hereinafter become evident.

Figure 1:
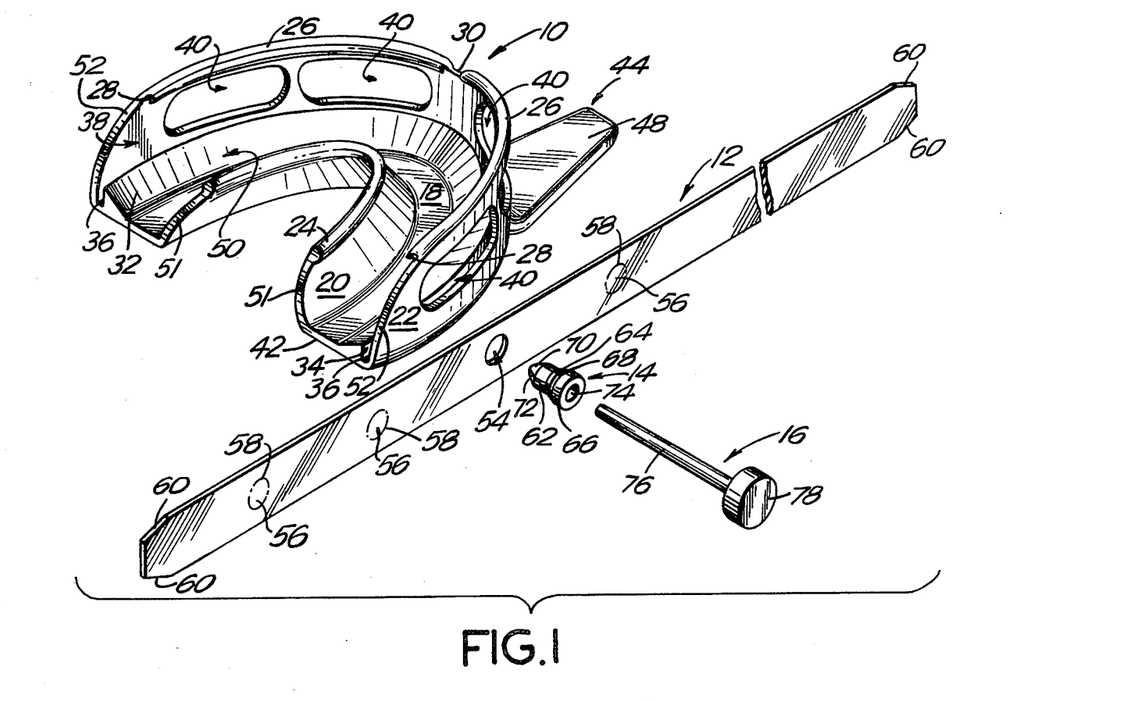
FIG. 1 is an exploded perspective view of the various parts of the dental impression tray assembly in accordance with the present invention.

The strap 12 is formed of flat flexible material, such as plastic, stainless steel, and the like, is adapted to provide spaced apart openings 54 therein. As shown at 56, the openings are of the knock-out type which require punching or knocking out of the particular material of the strap defined within a perforated circular perimeter 58. The distal edges of the strap are tapered at 60 to facilitate insertion of the strap 12 within the channel 38 provided on the interior of the sidewall 22. The thickness of the strap 12 is such as to be able to be received in the opposing slots 28, 36 provided adjacent the inner surface of the sidewall 22 so as to abut the inner surface of the sidewall when inserted into the channel 38.

The strap 12 can be adjustably slid through the channel 38 about the periphery of the sidewall 22 so as to suitably position any one or all of the transverse openings 54 in a position adjacent to a selected one or all of the elongated slots 40 in the impression tray. This will provide a through passage from the tray exterior to the interior of the dental tray, thus gaining access to the dental model or to a mold cavity created in the dental tray, as will hereinafter be defined.

Valve 14 includes a central shank portion 62 with an enlarged shoulder portion 64 and a further enlarged head portion 66. An annular peripheral groove 68 is formed about the valve proximate the junction between the shoulder portion 64 and the head portion 66. The forward end of the valve includes a tapered frustoconical tip 70 having a slit 72 formed therein to permit resilient opening and closing of the tip end. A bore 74 is formed entirely through the valve. The valve acts as a one-way valve, only permitting entry therethrough in the direction from the head portion 66 to the tip 70.

The sprue former 16 includes a longitudinal shaft portion 76 having a head portion 78 at one end thereof. The shaft 76 is sized to as to fit within the central bore 74 of the valve 14.

Referring now to FIGS. 5-10, utilization of the dental impression tray will now be described. Initially, a positive dental model 80 of the dental area is formed. Such positive model can be formed using standard techniques well-known in the dental art. For example, initially a negative impression is formed of the patient's mouth area. Then, from that negative impression, a positive model is formed. Other well-known methods of forming such a positive model can also be utilized.

Figure 5:
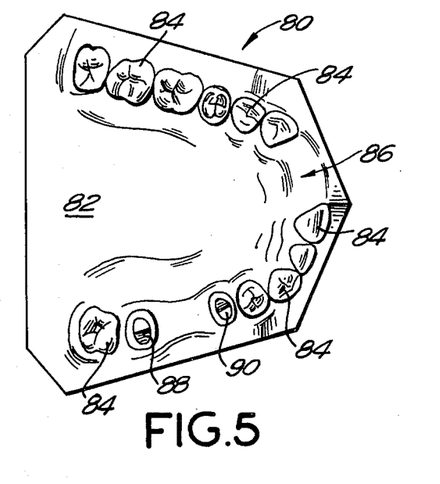
FIG. 5 is a top plan view of an unrestored positive dental model.

The positive model 80 typically includes a base 82 which is formed of a rigid material, such as stone or epoxy, but can also be formed of a flexible material, such as rubber, plastic and the like. As will hereinafter be explained, use of resilient material, such as rubber, would be preferable.

Formed on the base 82 of the laboratory cast positive model 80 are model teeth 84 representing the patient's existing teeth, and areas needing teeth restoration such as the missing teeth area 86, as well as an area between the model teeth 88 and 90 which requires bridge work, whereby the patient's teeth corresponding to model teeth 88, 90 have already been prepared for the bridge. Other types of dental areas needing restoration would also be included in the positive model.

Figure 6:
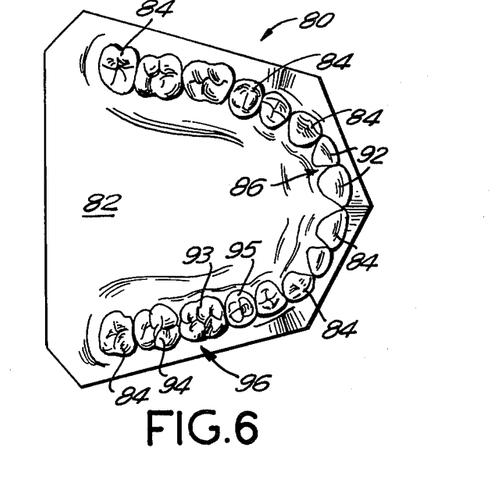
FIG. 6 is a view similar to FIG. 5, including the restored areas on the dental model.

The laboratory cast positive model 80 is then reconstructed so as to restore particular dental areas, as shown in FIG. 6. Specifically, the positive model 80 is shown to now include the two teeth 92 formed in the area 86, previously having teeth missing therefrom. Also, there is provided a restored tooth 93 disposed between two caps 94, 95 being secured on the model teeth 88 and 90 of the unrestored model shown in FIG. 5.

Once the positive model 80 has been restored, as shown in FIG. 6, the dental impression tray heretofore described, can be now utilized in conjunction with the positive model. Initially, the strap 12 is suitably placed within the channel 38 by sliding it between the grooves or slots 36, 28, so as to position it on the interior side of the outer sidewall 22. The strap 12 is positioned so as to locate a particular one of the transverse knockouts 56 adjacent the dental area whose impression is to be taken. The knockout 56 is then removed to expose the particular opening 54 therein. The valve 14 is then inserted through the selected transverse opening 54 so that the walls of the opening are engaged within the groove 68 of the valve. It should be noted, that the valve 14 also passes through the associated elongated locating slot or aperture 40, and through the channel 38 so as to extend into the interior of the dental tray 10.

Suitable dental impression material 97, such as silicone rubber, hydrocolloid and the like, is placed within the trough area 50 defined between the base wall 18 and the sidewalls 20, 22. The sprue former 16 may then be inserted through the central bore 74 of the valve 14 so as to not to extend into the dental impression material 97 at this time.

Figure 7:
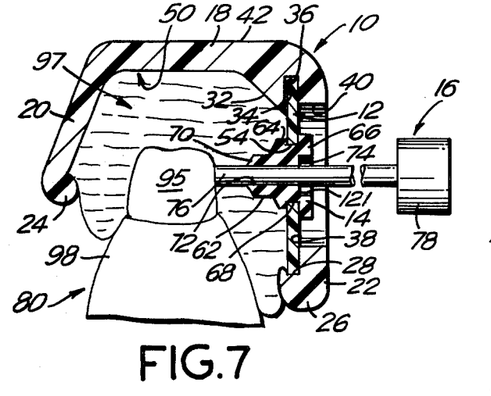
FIG. 7 is a cross sectional elevational view of a step in the utilization of the dental impression tray in accordance with the method of the present invention, showing the tray being positioned on the restored positive dental model.

The dental impression tray 10 is then placed over a portion of the laboratory cast positive model shown in FIG. 6. Specifically, the valve 14 is placed at an area that has been already restored by the laboratory. As shown, for illustration purposes, the valve 14 is placed at the restored cap 95 which has been mounted on the model tooth 90 in order to provide the bridge 96. It is noted, that the valve 14 could just as well been placed at the restored tooth 93, and another valve 14 could be placed at the restored teeth 92. The tray is pressed downward so as to cover the restored teeth, as well as covering the simulated gum area 98 formed on the positive model 80, with the impression material 97. The sprue former 16 is now further extended into the tray 10 so that the end of the shaft portion 76 abuts the edge of the restored cap 95, as shown in FIG. 7. A negative impression of the restored dental area on the positive model 80 is thus formed within the dental impression material 97, and the sprue former 16 may then be removed from the tray 10.

Figure 8:
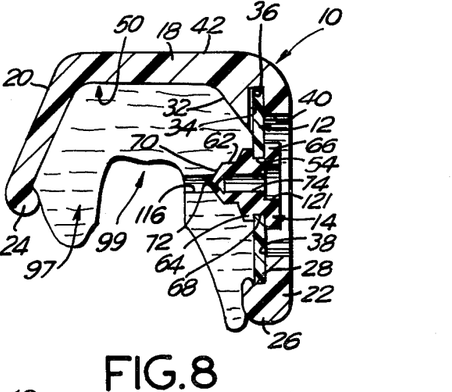
FIG. 8 is a cross sectional elevational view similar to that shown in FIG. 7, showing the tray removed from the dental model.

The dental impression tray 10, with the impression material 96 therein, is then removed from the positive mold to reveal the negative impression 99 formed in the dental impression material 96, as can be seen in FIG. 8. The dental impression tray is then set aside to permit the material to fully harden, as is well-known in the art. If desired, the sprue former 16 can now be removed from the tray 10, rather than before as set forth above, whereby this decision would depend upon the type of impression material used.

The model teeth and areas that have been restored in the positive model 80 are then uncovered so as to remove the laboratory tooth restoration to again revert the positive model 80 back to its state shown in FIG. 5. Thus, the specific restored tooth 93 and caps 94, 95 of the bridge 96 will be removed, and also the restored teeth 92 would be removed when a second valve 14 has been used for the teeth 92, so as to expose the tooth stumps 88, 90 previously prepared in the actual mouth area, and to expose the missing teeth area 86.

Figure 9:
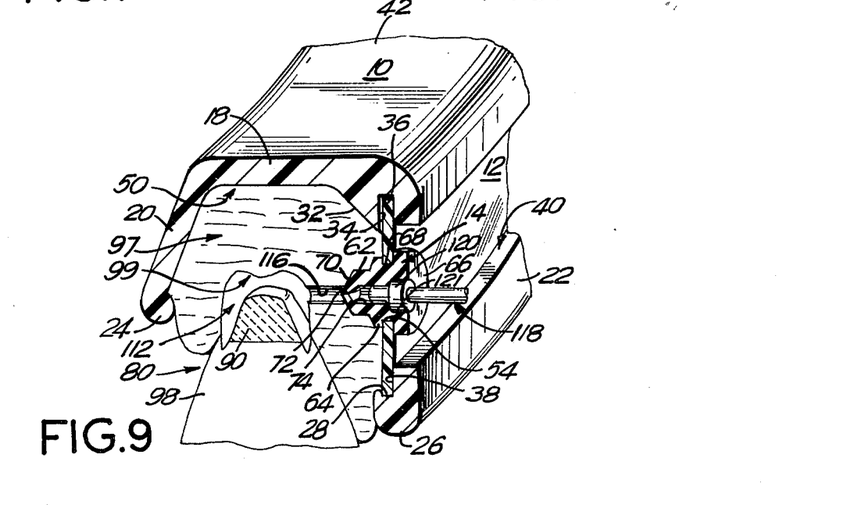
FIG. 9 is a perspective view, in cross section, similar to that shown in FIGS. 7 and 8, of a subsequent step in the formation of the dental prosthesis, showing the tray positioned on the unrestored positive dental model.

After the positive model 80 has been returned to its state shown in FIG. 5, the dental impression tray 12 is repositioned on top of the unrestored positive model, as shown in FIG. 9.

Figure 10:
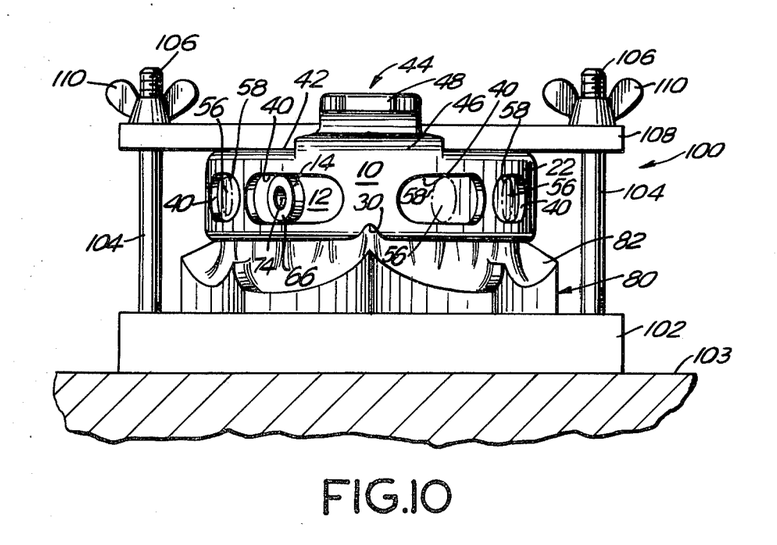
FIG. 10 is a side elevational view of a clamping device used to hold the tray of FIG. 9 in place over the unrestored positive dental model.

The dental tray 10 is clamped in place by means of any well-known clamp or holder, as typically shown in FIG. 10. As shown in FIG. 10, there is provided a clamping device 100 having a base 102 placed on a suitable support surface 103. A number of upstanding posts 104 having threaded distal ends 106 are embedded or secured within the base 102 in a conventional manner. A top plate 108 fits onto the posts 104 and are retained thereon by means of the wing nuts 110 which thread onto the ends 106.

The impression tray 10 is placed over the positive model 80 so that the base 18 has its rear surface 42 facing upwardly. As heretofore recited, the rear surface 42 is substantially flat so that the plate 108 can securely rest thereon and be tightly clamped in place onto the flattened surface 42. By tightening the wing nuts 110 downwardly onto the plate 108, the dental impression tray 10 is firmly seated upon positive model 80 therebeneath the base 82 of the positive model 80 being firmly disposed on the base 102 of the clamping device 100.

Referring again to FIG. 9, with the dental impression ion tray 10 properly seated upon the unrestored positive model 80, a mold cavity 112 is defined between the negative impression 99 formed previously, and the tooth stump 90 of the existing tooth area after the restoration has been removed. It should be noted, that after removal of the sprue former 16, a sprue channel 116 will remain formed in the dental impression material 97.

An injection nozzle 118 is now inserted into the valve 14. The nozzle 118 includes an outer collar 120 about the periphery of the nozzle. The collar 120 is retained by means of the countersink 121 of the bore 74. Thus, the countersink 121 forms a shoulder stop for the collar 120 to prevent complete insertion of the nozzle 118 into the valve 14, and only permits an end portion of the nozzle 118 to extend into the valve 14.

Figure 11:
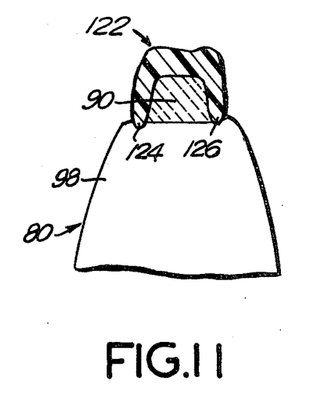
FIG. 11 is a cross-sectional elevational view showing the dental prosthesis formed onto the positive model with the tray having been removed.
Figure 12:
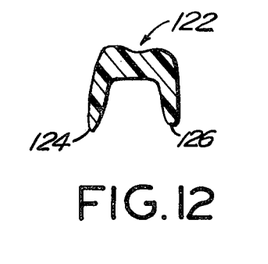
FIG. 12 is a cross-sectional elevational view of the dental prosthesis.

Suitable dental casting material is then injected through the nozzle 118 so that it passes through the sprue 116 and into the mold cavity 112, and fills the mold cavity so as to form the dental prosthesis shown generally as 122 in FIGS. 11 and 12. The dental prosthesis 122 will have the form of the dental prosthesis needed for covering the tooth stub 90, as well as the tooth stub 88 and forming the missing tooth 93 to provide the bridge 96.

The particular casting material that can be injected into the mold cavity would depend upon the use intended or stage of the dental prosthesis. For example, if the prosthesis is intended to be used as a temporary prosthesis, the typical dental material would include acrylic resin material, or other types of restorative material utilized for this purpose. On the other hand, the material could be a plastic or wax material, whereby the dental prosthesis 122 which is formed would only be the first stage, it being utilized as an investment pattern for a final casting, typically using the lost wax method. With the latter method, the final prosthesis could be formed of precious metal, or other like materials.

Since the particular dental prosthesis 122 is being formed on a positive dental model, types of material requiring high temperature can also be used. For example, polyvinylchloride, which normally requires approximately 800° F. to set, can be utilized as the casting material and the entire process can be carried out under such high temperature.

Once the dental prosthesis 122 has hardened, the dental impression tray 10 can be removed to expose the dental prosthesis 122, as shown in FIG. 11. If the positive dental model 80 was made of rubber or other pliable material, as heretofore mentioned, it will be easy to remove the prosthesis 122 without having to cut or break apart the dental model 80. In this way, the entire dental prosthesis 122 can be removed without cutting the dental model 80 in the areas adjacent to the lower prongs 124, 126 intact. These prongs are important in the actual dental prosthesis since these prongs must be inserted and fit within the actual gum area in order to have a proper prosthesis.

The dental prosthesis 122 is shown in FIG. 12. As heretofore mentioned, it can either be a temporary prosthesis, a permanent prosthesis, or can be a model for a further stage in the forming of a final dental prosthesis.

Figure 13:
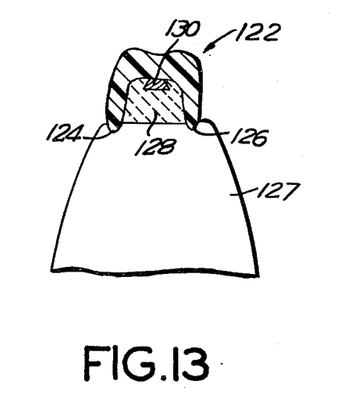
FIG. 13 is a cross-sectional elevational view shwoing the dental prosthesis applied directly onto the dental area in the patient's mouth.

As shown in FIG. 13, once the prosthesis 122 has been formed, it can be inserted directly into the patient's mouth area. The prosthesis 122 is placed directly onto the patient's gum area 127 and sits suitably on top of the patient's teeth, as shown for example, on the patient's prepared tooth stump 128. It is noted that it suitably fits accurately on top of the tooth stump 128 and the other associated teeth to form the required bridge mentioned above. Another prosthesis would be formed for the other missing teeth in the patient's mouth which are located in other spaced-apart areas of the mouth.

If desired, a splint 130 could be placed on top of, or inserted within a channel formed in the tooth stump 128, prior to fitting of the dental prosthesis 122. Once the prosthesis 122 is suitably securely positioned in place on top of the teeth, the splint 130 will be inherently secured so as to provide additional support for the tooth area which is being restored.

Should the dental prosthesis 122 be either the temporary or permanent prosthesis, suitable coloring material can be added prior to casting of the prosthesis 122. The coloring material would be placed on the inner surface of the negative impression 99, and when the casting material is injected into the mold cavity, the coloring material would be dispersed into the surface of the casting material so that the coloring material will provide the outer color tone of the dental prosthesis, realistically matching the other natural teeth in the patient's dental tooth area.

When the dental prosthesis is removed from the tray 10, it may be necessary to slightly grind down the sprue formation or tang that remains on the side of the prosthesis 122 which is formed by the sprue channel 116. However, by utilizing the shoulder stop formed by the countersink 122 in the valve 14, the extent of penetration of the injection nozzle 118 is limited by the collar 120, and this prevents flow back of the casting material. Also, it leaves the above-mentioned tang on the dental prosthesis which can be easily removed. However, the tang is preferable to an indent in the prosthesis which might otherwise be formed if the nozzle 118 was permitted to be positioned fully in the sprue channel 116 to form a part of the wall of the negative impression 99.

The dental impression tray 10 of the present invention is preferably fabricated from a suitable plastic material, wherein the tray is molded in a conventional manner well-known in the art. However, the tray 10 includes undercuts therein, such as the peripheral groove 36. These undercuts complicate the molding process for forming the tray, in addition to increasing the manufacturing costs thereof. Therefore, the impression tray has been modified as shown in FIGS. 14 and 15.

Figures 14, 15, 16:
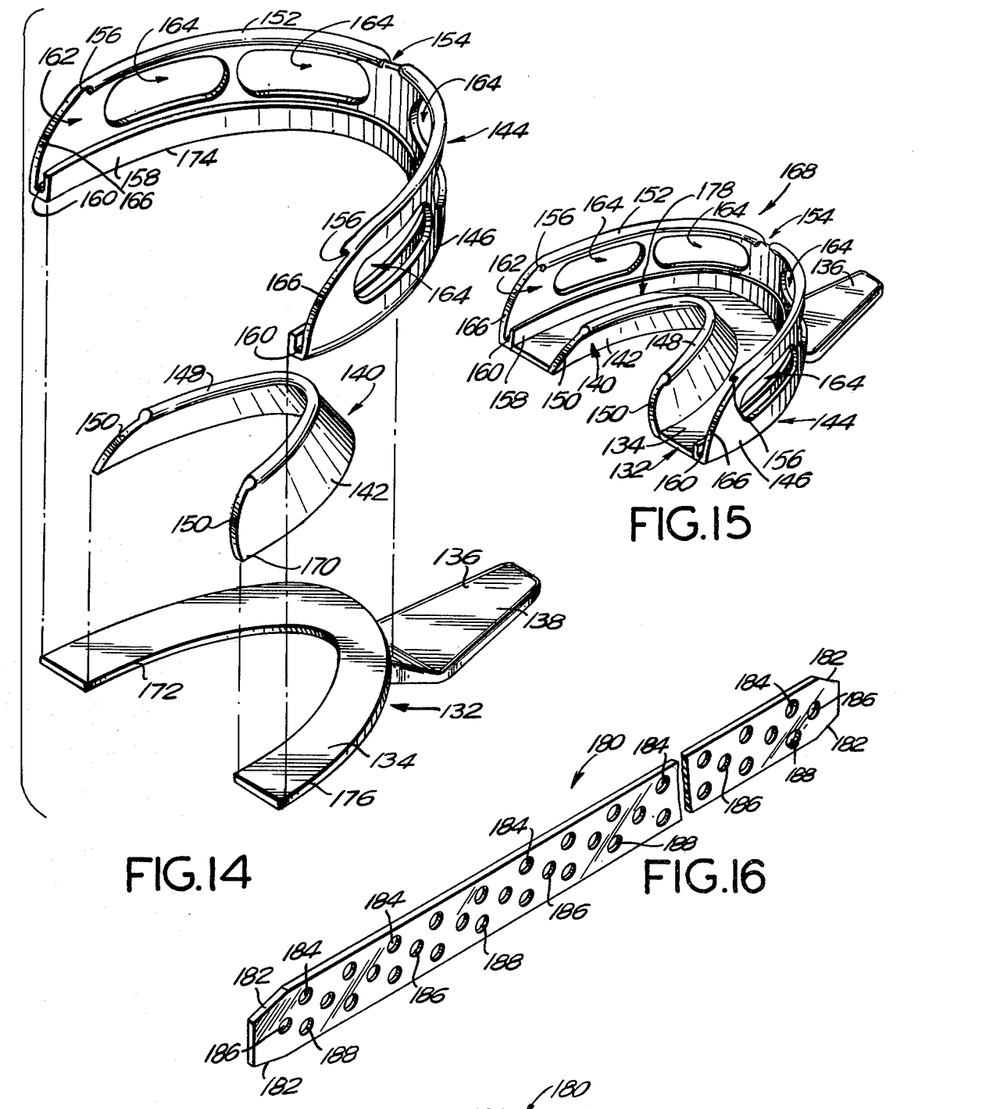
FIG. 14 is an exploded perspective view of sections of a modified dental impression tray in accordance with the present invention.
FIG. 15 is a perspective view of the modified dental impression tray formed from the sections shown in FIG. 14.
FIG. 16 is a fragmented perspective view of a modified strap in accordance with the present invention.

FIG. 14 shows the modified tray divided into three separate sections, so that each of these sections can be molded separately, and then joined together to form the modified tray. The body section 132 includes a base wall 134 and a handle 136, similar to handle 44, which is integrally formed with and extends from the base wall 134. The handle 136 includes a tapered handle portion 138 for grasping of the tray, the handle portion 138 is secured to a bottom surface of the base wall 134.

The inner upstanding section 140 provides the inner sidewall 142. The outer upstanding section 144 provides the outer sidewall 146. Accordingly, the inner sidewall 142 is similar to the above-mentioned inner side wall 20, including a reinforced rib 148 at its upper end and terminating in arcuate edges 150 as the forward distal ends thereof. The outer sidewall 146 is likewise similar to the above-mentioned outer sidewall 22, including an inwardly directed overhanging lip 152 at the upper end thereof divided by a notch 154 at the midpoint thereof. The lip 152 provides a peripheral groove 156 along the inside of the sidewall 146.

An upwardly directed flange 158 is provided around the lower end of the outer wall 146 to define a peripheral groove 160 along the bottom inside of the sidewall 146. Thus, the grooves 156 and 160 linearly extend along the entire inner periphery of the outer sidewall 146 to define therebetween a channel 162 similar to the above-mentioned channel 38. Accordingly, elongated locating slots 164 are positioned longitudinally along the outer sidewall 146 in similar manner as the above-mentioned slots 40. Furthermore, the forward distal ends of the outer sidewall 146 terminate in arcuate edges 166 to facilitate the insertion of the strap 12 within the channel 162 in the same manner as mentioned above.

Thus, when the three sections 132, 140, and 144 are joined together in a conventional manner using suitable securing or adhesive means, the assembled sections form the modified tray 168 as shown in FIG. 15, the modified tray 168 being similar to the above-mentioned tray 10. As shown, the lower outer edge portion 170 of the inner section 140 is secured to the inner arcuate edge 172 of the base wall 134 of the body section 132, and the lower inner edge 174 of the falnge 158 of outer section 144 is secured to the outer arcuate edge 176 of the base wall 134 of the body section 132. The three assembled sections defining the tray 168 provide a trough-like area 178, which can receive the above-mentioned dental impression material 97 therein for the formation of the negative impression 99. Accordingly, the tray 168 can receive the above-mentioned strap 12 therein in the same manner as set forth above, or can receive a modified strap as set forth below.

FIG. 16 shows the modified strap 180 formed of flat flexible material, preferably plastic. The strap 180 has the same overall dimensions as the above-mentioned strap 12, including tapered distal edges 182 to facilitate insertion of the strap 180 into either of the above-mentioned channels 38, 162 of the trays 10, 168 respectively. Accordingly, the selected thickness of the strap 180 permits the upper and lower edges of the strap to be received in the opposing grooves 28, 36 or 156, 160 in the sidewalls 22 or 146 of the trays 10, 168 respectively.

A plurality of openings are provided in the strap 180, there being three longitudinally extending rows of openings 184, 186, and 188. The openings in one row are alternatingly arranged with respect to the openings of the adjacent row, so that the openings 184, 188 of the outer rows are in transverse alignment with each other, and the openings 186 of the middle row are longitudinally spaced on either side of the openings 184, 188.

Figure 17:
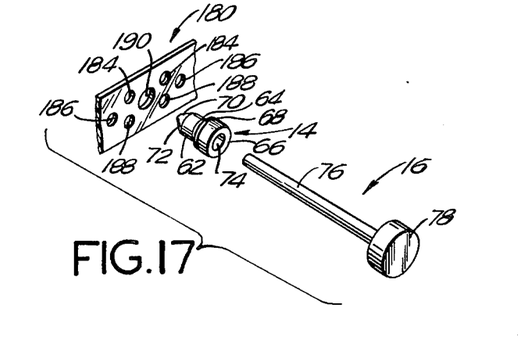
FIG. 17 is a fragment exploded perspective view of the modified strap of FIG. 16, and the one way valve and sprue former associated therewith.

With this arrangement of the openings 184, 186, 188, any one of the openings can be sufficiently expanded, such as by cutting around the selected opening, to provide an enlarged opening 190. Accordingly, the enlarged opening 190 is made equal in size to the above-mentioned opening 54 of the strap 12, so that the enlarged opening 190 can receive the valve 14 therein, with the walls of the enlarged opening 190 being engaged in the peripheral valve groove 68 in the manner set forth above.

Once the valve 14 is secured in the strap 180, the sprue former 16 can be inserted into the bore 74 of the valve 14, wherein the procedure that follows would be the same as set forth above.

In addition to providing the dentist or laboratory technician with a greater number of locations for positioning the valve 14 in the dental impression tray, the openings 184, 186, 188 further function to receive the dental impression material 97 therein when the negative impression 99 is being formed. Thus, the impression material 97 is secured to the strap 180 by means of filling these openings in the strap, thereby insuring that the impression material 97 is removed from the dental model 80 in the above-mentioned process. It is noted, that the ridges 24, 148 on the inner sidewall and the lip 26, 152 on the outer sidewall also insure the removal of the impression material 97 with the trays 10, 168 respectively.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental impression tray for use in forming a dental prosthesis, comprising:
   an arcuate tray having a substantially U-shaped cross sectional configuration to define a trough in which is placed dental impression material for the formation therein of a negative impression of a restored area of a dental model;
   valve means for adjustable placement in said arcuate tray with respect to a mold cavity defined between the negative impression and the unrestored dental model, and for application of casting material into the mold cavity;
   said arcuate tray including a base wall, and upstanding inner and outer sidewalls;
   a retaining channel provided adjacent said outer sidewall;
   longitudinally spaced apart elongated slots provided in said outer sidewall in communication with said channel; and
   said valve means extending from a selected one of said slots through said channel and into said trough.

2. A dental prosthesis tray as in claim 1, wherein an upper end of said outer sidewall includes an inwardly directed overhanging lip, and further comprising a retaining wall upwardly extending from said base wall and inwardly spaced from said outer sidewall, said lip and retaining wall defining said channel therebetween.

3. A dental prosthesis tray as in claim 1, wherein said tray includes three sections integrally joined together to provide said tray, one of said sections providing said base wall, a second sections providing said inner sidewall, and the third section providing said outer sidewall.

4. A dental prosthesis tray as in claim 3, wherein said third section includes an inwardly directed overhanging lip disposed around an upper end thereof, and an upwardly directed flange provided around a lower end thereof, said lip and flange defining said channel therebetween.

5. A dental impression tray as in claim 3, and further comprising a clamping device for clamping said dental impression tray onto the unrestored dental model, said clamping device engaging a flat outer surface of said base wall of said tray.

6. A dental impression tray as in claim 1, wherein said valve means includes a one way valve having a central bore therethrough, and further comprising a removable plug insertable in said central bore of said valve and extendable to said mold cavity for providing a sprue channel in the negative impression material.

7. A dental impression tray as in claim 6, and further comprising a strap member adjustably slidable in said channel, and at least one opening provided in said strap member for alignment with said selected one of said slots, said strap opening receiving said valve and positioning said valve within said one slot.

8. A dental impression tray as in claim 7, wherein said one way valve comprises a shank portion, and an annular groove formed about said shank portion to snap-fit into said opening of said strap member.

9. A dental impression tray as in claim 7, wherein said opening is provided by a knock out hole.

10. A dental impression tray as in claim 7, wherein said strap member includes retaining means to secure the dental impression material to said tray, said retaining means including a plurality of openings in said strap member, one of said plurality of openings defining said valve receiving strap opening.

11. A dental impression tray as in claim 10, wherein said plurality of openings are arranged in longitudinal rows with the openings of one row being alternatingly disposed with respect to the openings of an adjacent row.

12. A dental impression tray as in claim 6, and further including a shoulder stop provided in said bore of said valve for limiting the insertion depth into said valve of an injection nozzle which applies the casting material, said injection nozzle including a collar thereon for engagement with said shoulder stop.

13. A dental impression tray as in claim 1, wherein said inner sidewall is imperforate to retain the dental impression material in said trough, said slots being provided only in said outer sidewall.

14. A method of forming a dental prosthesis comprising:
    forming a positive dental model of a dental area to be restored;
    said positive dental model being formed of pliable material so that the dental prosthesis can be removed without destroying the positive dental model;
    making the restoration on the dental model;
    forming a negative impression in a dental impression tray of the restored area of the dental model;
    removing the restoration from the dental model;
    repositioning the dental impression tray having the negative impression therein on the unrestored dental model to form a mold cavity between the negative impression and the unrestored dental model;
    injecting dental casting material into the mold cavity to form a dental prosthesis; and
    removing the dental prosthesis from both the unrestored dental model and the impression tray.

15. A method as in claim 14, and further comprising the step of placing the dental prosthesis in the dental area being restored as a final dental prosthesis.

16. A method as in claim 14, and further comprising the step of utilizing the dental prosthesis as an investment model for further casting of a final dental prosthesis.

17. A method as in claim 14, wherein said dental prosthesis includes undercuts formed into the model material.

18. A method of forming a dental prosthesis comprising:
    forming a positive dental model of a dental area to be restored;
    making the restoration on the dental model;
    inserting a valve in a dental impression tray;
    placing a shaft through the valve and extending it to the restored dental area so as to form a sprue channel extending from the valve to the restored dental area;
    removing the shaft;
    forming a negative impression in the dental impression tray of the restored area of the dental model;
    removing the restoration from the dental model;
    repositioning the dental impression tray having the negative impression therein on the unrestored dental model to form a mold cavity between the negative impression and the unrestored dental model;
    using the valve and sprue channel for injecting dental casting material into the mold cavity to form a dental prosthesis; and
    removing the dental prosthesis from both the unrestored dental model and the impression tray.

19. A method as in claim 18, and further comprising the step of placing the dental prosthesis in the dental area being restored as a final dental prosthesis.

20. A method as in claim 18, and further comprising the step of utilizing the dental prosthesis as an investment model for further casting of a final dental prosthesis.

* * * * *